(12) United States Patent
Birke et al.

(10) Patent No.: US 7,923,591 B2
(45) Date of Patent: Apr. 12, 2011

(54) METHOD AND DEVICE FOR PRODUCING LOWER OLEFINS FROM OXYGENATES

(75) Inventors: Gerhard Birke, Frankfurt am Main (DE); Harald Koempel, Neu-Isenburg (DE); Waldemar Liebner, Oberursel (DE); Hermann Bach, Heiligenroth (DE)

(73) Assignee: Lurgi AG, Frankfurt am Main (DE)

( * ) Notice: Subject to any disclaimer, the term of this patent is extended or adjusted under 35 U.S.C. 154(b) by 826 days.

(21) Appl. No.: 11/718,037

(22) PCT Filed: Oct. 27, 2005

(86) PCT No.: PCT/EP2005/011530
§ 371 (c)(1),
(2), (4) Date: Sep. 4, 2007

(87) PCT Pub. No.: WO2006/048184
PCT Pub. Date: May 11, 2006

(65) Prior Publication Data
US 2009/0137856 A1    May 28, 2009

(30) Foreign Application Priority Data
Nov. 2, 2004  (DE) .......................... 10 2004 052 828

(51) Int. Cl.
C07C 1/24    (2006.01)

(52) U.S. Cl. ........ 585/639; 585/640; 585/807; 585/809; 208/313; 208/322; 208/332; 208/333; 203/25; 203/81

(58) Field of Classification Search ................... 585/860, 585/862, 864, 639, 640, 807, 809; 208/313, 208/322, 332, 333; 203/25, 81
See application file for complete search history.

(56) References Cited

U.S. PATENT DOCUMENTS

| 4,447,318 A * | 5/1984 | Ogura et al. ................. 208/348 |
| 2003/0139635 A1 * | 7/2003 | Hack et al. ..................... 585/609 |
| 2003/0199722 A1 * | 10/2003 | Lattner et al. ................. 585/809 |

FOREIGN PATENT DOCUMENTS

| DE | 100 27 159 A1 | 12/2001 |
| WO | 01/92190 A | 12/2001 |

* cited by examiner

Primary Examiner — Prem C Singh
(74) Attorney, Agent, or Firm — Norris McLaughlin & Marcus PA

(57) ABSTRACT

Method and device for manufacturing at least one low olefin from an oxygenate-containing first reaction mixture (11) through conversion by a catalyst (20) to an olefin and paraffin-containing second reaction mixture (21) where the second reaction mixture (21) is flowed through a separation system (300), in which one at least one low olefin-containing first product stream (31) and at least one paraffin-enriched fraction (321) is extracted and where the remaining product stream (322) is at least partially recirculated to the catalyst (20).

21 Claims, 3 Drawing Sheets

METHOD AND DEVICE FOR PRODUCING LOWER OLEFINS FROM OXYGENATES

This is a 371 of PCT/EP2005/011430 filed 27 Oct. 2005 (international filing date).

The invention concerns a method and a device for manufacturing lower olefins from oxygenates.

In the underlying method, the target product Propylene is obtained from Methanol by means of the so called "Gas to Chemicals"—Route (GTC), which is obtained by means of a method developed by the applicant, entitled "Lurgi Mega-Methanol"® through conversion of natural gas, by means of the so called "Methanol to Propylene" method (MTP®), also developed by the applicant.

BACKGROUND OF THE INVENTION

A method of the type mentioned above is known from DE 100 27 159 A1, where methanol vapor is converted into a dimethylether (DME) containing vapor mixture in a first catalyst from which a propylene-containing first product mixture is created based on a form selective Zeolite catalyst. From this, a 99.5 percent by volume propylene-containing product stream is extracted through a separation system while the remaining products are carried separately or can also be partly recirculated again in the form-selective Zeolite catalyst for renewed conversion.

It is unfavorable that in the most recent background art, recycling of the remaining products for renewed conversion in the Zeolite catalyst is only ineffectively possible.

Therefore, the basic objective of the invention is to continue developing a method and a device of the type mentioned in the beginning in such a way that the recycling of the remaining products in the manufacturing of lower olefins can be carried out effectively.

SUMMARY OF THE INVENTION

According to the invention, the objective in a method for manufacturing lower olefins from a first reaction mixture containing oxigenates to a second reaction mixture containing olefins and paraffins through conversion by a catalyst, whereby the second reaction mixture is processed through a separation system by which a first product stream containing a lower olefin is created and then the remaining product stream is at least partly fed to the catalyst, is achieved in that in the separation system from the second reaction mixture at least a paraffin-rich fraction is extracted which is not fed to the catalyst.

DETAILED DESCRIPTION

Lower olefins are preferably propene, but also ethene and butene. Oxygenates are preferably methanol and dimethylether created from it by means of a dehydrating catalyst. Also conceivable are higher alcohols or their simple or mixed ether. In sub-ordinate parts, a series of other oxygenates including ketones and ester can be present which are contained as by-products in the alcohols or created in the catalyst and recirculated. To date, no differentiation according to paraffins and olefins has been made in the stream recirculated to the catalyst. However, it has been shown that the paraffins can hardly be converted from the catalyst and thus concentrate themselves in the recirculation as inerts. Therefore, a part of the total flow in the recirculation has to be continuously removed from it to prevent the concentration of the inerts. With the partial removal of the flow in the recirculation, the parts which are convertible in the catalyst are also removed from the recirculation.

Through separation of the paraffins before recycling of the remaining product stream in the separation system, it becomes possible to minimize the circulation of inerts in the recirculation cycle and to increase the share of substances convertible in the catalyst. Based on this, they need not be partly removed together with the inerts as was the case to date, but become available for conversion in the target product. Thus an increase of the quantity of the low olefins to be manufactured becomes possible by using the same amount of first reaction mixture.

The separation facility advantageously contains a paraffin-olefin separation stage downstream of the separation of the lower olefins-containing first product stream. This has the advantage that for the paraffin separation through the paraffin-olefin separation stage an already increased concentration of the paraffins becomes available.

Generally the second reaction mixture obtained through conversion at the catalyst also contains small parts of oxygenates, which are created as by-products in the catalyst. These are also each fed back at least partially to the catalyst with the remaining product stream together with the Hydrocarbon fractions. On the one hand, this has the advantage that these oxigenates can also be converted to the desired lower olefins at the catalyst and can thus increase the output. On the other hand, it has the advantage that the oxigenates thus fed back for renewed conversion do not contaminate the paraffin-rich fractions extracted from the circulation so that their further utilization is simplified.

Further than this the objective mentioned above according to the invention in a second method for the manufacture of lower olefins from a first reaction mixture containing oxigenates through conversion in a catalyst to an olefin and paraffin-containing second reaction mixture is achieved in that the second reaction mixture is flowed through a first separation stage, in which a lower olefin-containing first product stream and a higher olefin and paraffin-containing second product stream are separated whereby from the second product stream the higher boiling hydrocarbons are removed through a second separation stage and from the remaining third product stream a paraffin-rich fraction is extracted through an extractive distillation by the use of a selective polar solvent and whereby the remaining fourth product stream is at least partially fed back to the catalyst.

Through the thus described operation the advantages already mentioned above become further enhanced. In this, the paraffin-rich fraction of a very high purity can be created so that it is not prepared expensively but can be provided directly for commercial utilization.

The separation of higher boiling hydrocarbons compared to the full mixture by means of the second separation stage has the purpose that aromatics are removed from recirculation to a large extent. With respect to olefin formation, aromatics behave inert in the catalyst. However, they react with substituted aromatics, thereby using the oxygenates contained in the first reaction mixture and because of this they are undesirable in the feed back streams. Besides this the aromatics can damage the catalyst through recarburizing. The aromatics also occupy the effect of the selective polar solvent in a subsequent extractive distillation and thus limit the effect of the solvent on the olefins. As a result, by separating the aromatics, it is possible to save solvent.

According to a further development of the invention it is planned that through the second separation stage a hydrocarbon fraction of medium boiling range is removed from the second product stream so that this is not fed to catalyst.

Through this a part of the flow planned for recirculation is removed. Thus it is secured that the inerts which cannot be removed together with the paraffin-enriched fraction at the extractive distillation are partly removed again from recirculation cycle and thus do not concentrate themselves substantially in this.

Through a suitable division of the easily boiling hydrocarbon fractions in the third product stream and the hydrocarbon fraction of medium boiling range in the separation device it is secured that only the part of the hydrocarbon is carried to the extractive distillation, which is supposed to be separated. In this the hydrocarbon fraction of medium boiling range can also be partly or fully fed back to the catalyst directly.

A first olefin-enriched fraction can be removed from the fourth product stream particularly advantageously through a further distillation and from the remaining fifth product stream a second paraffin enriched fraction can be removed through a second extractive distillation by using a selective polar solvent and the remaining sixth product stream as well as the first olefin-enriched fraction is at least partially fed back to the catalyst. It is sensible to remove the solvent by means of a solvent stripper from the sixth product stream before recirculating it to the catalyst and to re-add it to the extractive distillation.

Part of the hydrocarbon fraction of medium boiling range, which was removed through the second separation stage from the second product stream, can be given together with the fifth product stream to the second extractive distillation.

Through the multi-step separation process a further paraffin-enriched fraction is removed from recirculation. This can also be of such high purity that it can be directly used commercially or can be prepared for that with only minimal expenses. Additionally, the share of the quantity taken out from the recirculation by means of the second separation stage can be limited. Similarly, the share of the different fractions which are removed from the circulation can be adjusted to the output structure of the catalyst and thus the complete circulation can be optimized.

Advantageously, the solvent in the product streams after the first and second extractive distillation is extracted with a common solvent stripper after the second extractive distillation from the sixth product stream and re-added to the first and second extractive distillation from the common solvent stripper. The division of the solvent to both extractive distillations is based on the type and the desired separation of the hydrocarbon fractions. It shows that in the distillation of the fourth product stream the composition of the obtained first olefin-enriched fraction is mainly independent of the presence of solvent and that this is obtained free from the solvent because of the boiling range. Therefore, the removal of the solvent from the fourth product stream can be done away with and the common solvent stripper after the first extractive distillation in the fourth product stream is not necessary. Thus a common solvent stripper can be used after the second extractive distillation in the sixth product stream. This leads to cost advantages for the system.

In a similar way through a further extractive distillation step each and a distillation done afterwards, a further paraffin-enriched and an olefin-enriched fraction with respective high boiling range can be obtained, if this is possible on economic grounds. In this in similar fashion a common solvent stripper can be used. In this the paraffin-enriched fractions are correspondingly removed from the circulation while the olefin-enriched fractions are correspondingly fed back to the catalyst again.

Advantageous is the selective solvent N-Methylpyrrolidone (NMP) which gives paraffins a higher volatility than olefins of the same hydrocarbon atomic number.

In addition, there are also other suitable selective polar solvents, in whose solution paraffins have a higher volatility than olefins. Thus for example: butyrolactone, Nitriles such as Acetonitrile, Propionitrile, Methoxypropionitrile, Ketones such as Acetone, Furfurol, N-alkyl substituted lower aliphatic acid amide, such as Dimethylformamide (DMF), Diethylformamide, Dimethylacetamide (DMAC), Diethylacetamide, N-Formylmorpholine (NFM), N-alkyl substituted cyclic acid amide (Lactame) such as N-Alkylpyrrolidone in general, in particular N-Methylpyrroldone. Generally N-alkyl substituted lower aliphatic acid amide or N-alkyl substituted cyclic acid amides are used. However, mixtures of these solvents among which e.g. of N-Methylpyrrolidone with Acetonitrile, mixtures of these solvents with water and/or with ethers, e.g. Methyl-tert-butyl ether, Ethyl-tert-butyl ether, Propyl-tert-butyl ether, n or iso-Butyl-tert-butyl ether, or with Tetrahydrofuran can also be used.

Because the selectivity of NMP regarding olefins is relatively low in comparison to paraffins, the ratio of olefins to NMP should be set to about 1 to 10 or more.

In this, it is particularly advantageous to add Ethylene glycol (EG) to the selective solvent, while water is added during the second extractive distillation. Water can also be added to the real extractive distillation columns and also to the corresponding solvent stripper.

Instead of ethylene glycol, other glycol mixtures are also usable. The glycol mixture can also form selective polar solvents itself.

In the catalyst, lower boiling oxigenates such as for example acetone, ethanol or methyl formate are also produced in small quantities. Similar to the higher olefins, these are also converted to the desired lower olefins during recirculation by the catalyst. It is therefore desirable to re-feed these oxygenates to the catalyst. Through the presence of EG and water, the polar oxigenates are bound to water and water is bound to EG. As a result, the oxygenates become less volatile and are extracted not together with the low boiling paraffin-enriched fraction, but with the somewhat higher boiling sixth product stream and can be fed to the catalyst. The rest of the oxigenates in the solvent circulation can be removed by means of the common solvent regeneration. Through this the feed back circulation is optimized completely.

Advantageously the water to be added to an extractive distillation, mentioned above, can be extracted from the first separation stage. This is sensible as in the first separation stage water accumulates regardless and thus a self-supply of water for the extractive distillation is unnecessary.

Preferably the oxigenates in the first reaction mixture contain dimethylether and water while the catalyst is a form-selective Zeolite catalyst of the Pentasil type whereby the oxigenates are created at least partly by means of a dehydrating catalyst from methanol and the desired lower olefin is propylene.

According to the invention the above mentioned objective is further achieved through a device for the manufacturing of at least a lower olefin from one oxigenate-containing first reaction mixture with a catalyst for converting into an olefin and paraffin-containing second reaction mixture and with a separation system connected with the catalyst for creating at least a lower olefin-containing first product stream and a remaining product stream and with a feedback device between the separation system and the catalyst for the remaining product stream whereby the separation system has a paraffin-olefin separation device and the paraffins separated with it are not taken to the feedback device.

Through such a device the above-mentioned advantages are further enhanced.

BRIEF DESCRIPTION OF THE DRAWINGS

In the following, the invention is clarified in detail through schematic diagrams. They show:

FIG. 1 shows a flow diagram with a DME Reactor (10), a catalyst containing MTP Reactor (20) and a separation system (300), which contains an olefin-paraffin separation facility (500).

Figure 1:
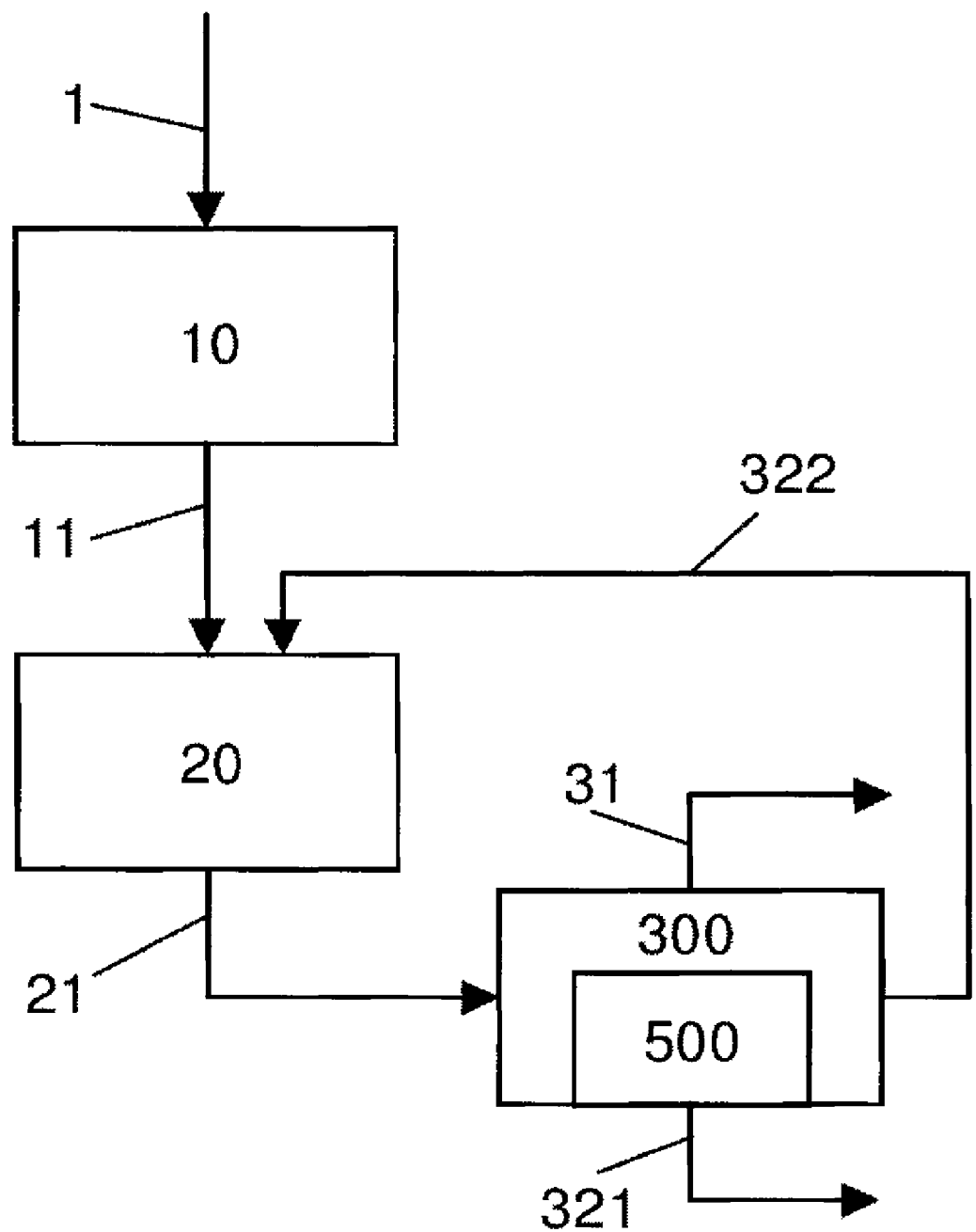
FIG. 1 a flow diagram of the method and the device in principle.

Methanol (1) is fed into the DME Reactor (10) as overheated vapor at about 260° C. The DME Reactor is a single step reactor in which the substantial portion of the introduced methanol vapor is, for example, dehydrated to a first reaction mixture (11) of dimethylether (DME) and water by means of an Aluminum oxide catalyst ($\gamma$-$Al_2O_3$) according to the following reaction equation outlined in U.S. Pat. No. 3,058,576:

$$2CH_3OH \rightarrow CH_3OCH_3 + H_2O$$

The mentioned catalyst has high activity and high selectivity and soon reaches thermodynamic equilibrium. The reaction is exothermic and the reaction equilibrium is largely independent of the reaction pressure. The heat creation through the conversion in the DME Reactor (10) is reduced in the subsequent MTP Reactor (20) whereby its effectiveness is increased. Therefore, the DME Reactor (10) is meaningful yet not necessary in all cases. Besides methanol a mixture of methanol, DME and water can also be fed into the DME Reactor as a recycle stream from the system.

The obtained first reaction mixture (11) at a temperature of about 440° C. is fed into the so-called MTP Reactor (20), which contains a catalyst and converts the first reaction mixture (11) to an olefin-containing second reaction mixture (21). The catalyst (20) is, for example, a poured, granular form-selective Zeolite catalyst of the Pentasil type such as is known from EP 448 000 B1. It consists of an aluminum silicate with an Al/Si atomic ratio of at least 10, whose primary crystallites have an average diameter of 0.1 to 0.9 µm. At least 20% of them are combined into agglomerates of 5 to 500 µm, where the primary crystallites or agglomerates are combined through fine particle aluminum oxide and where the BET surface area is 300 to 600 m²/g, the pore volume (determined according to mercury porosimetry) is 0.3 to 0.8 cm²/g and the quantity of the aluminum oxide binding agent is 10 to 40 weight-% with reference to the end product and where the catalyst is provided in H-shape. Normally the pressure in the region of the catalyst is in the range of 1.2 to 2.0 bar. The temperature of the reaction at the catalyst lies advantageously at about 480° C. The Reactor can be designed with one or several catalyst steps where the supply to the individual catalyst steps can be provided from the previous step or directly from the common supply.

Advantageously, process water from the separation system can be recirculated to the MTP Reactor. This can be meaningful because the additional supply of water to the MTP Reactor can optimize the partial pressure of the used mixture for the conversion. This generally also applies to the additional supply of substances which cannot be converted in the catalyst.

The catalyst has the property that it converts not only the oxigenates DME or methanol in olefins, but also olefins into olefins of lower carbon number. The last mentioned property is used to increase the effectiveness of the conversion by means of qualified recirculation of olefins with higher number of carbon than the desired propylene.

The second reaction mixture (21) obtained from the MTP Reactor normally contains water, olefins, paraffins, DME, other hydrocarbons and other oxigenates.

This second reaction mixture (21) is fed into a separation system (300). The separation system separates a first product stream (31), which mainly consists of a lower olefin, which is the desired valuable product propylene in this example. The separation system takes a further part of the used second reaction mixture (21) as remaining product stream (322) back to the catalyst containing MTP Reactor (20). Because this product stream contains parts which can be converted into the desired valuable product by means of the catalyst or positively influence the reaction, the effectiveness of the method and the system is increased based on this recirculation.

The separation system features a paraffin-olefin separation stage (500), which takes out a paraffin-rich fraction (321) from the recirculation cycle. Normally a part is taken out from a not fully processable back flow so that the back flow does not continuously increase. Paraffins are a part in the second reaction mixture (21), which cannot be converted in the catalyst anymore and are present in mentionable quantity in the second reaction mixture (21). Therefore, the selective removal of paraffins above all has proven to be particularly effective for the complete process.

Figure 2:
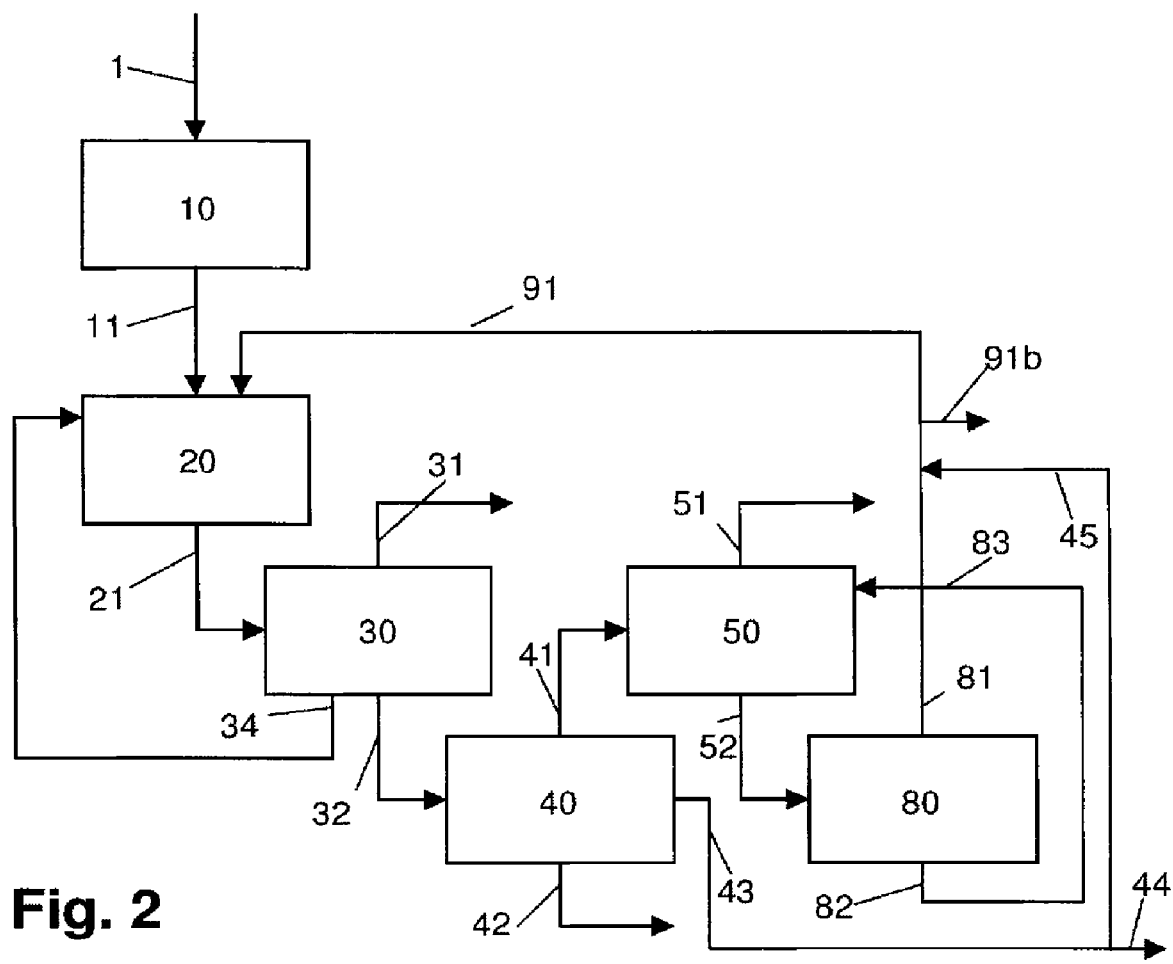
FIG. 2 a flow diagram of the method and the device with an extractive distillation, FIG. 3 a flow diagram of two extractive distillation units.

FIG. 2 shows a flow diagram similar to FIG. 1, where the separation system (300) including the paraffin-olefin separation stage is shown in more detail. The catalyst containing MTP Reactor (20) includes a first separation stage (30), a second separation stage (40) and an extractive distillation (50) with a solvent stripper (80).

The second reaction mixture (21) from the MTP Reactor is taken to a first separation stage (30) which removes the valuable substance propylene-containing first product stream (31). In addition, the first separation stage (30) separates the water contained in the reaction mixture (34), which is taken to the MTP Reactor (20). Part of the water is removed from the circulation process in a way not shown here. The remaining second product stream (32) is fed into a second separation stage (40).

For the water separation, the first separation stage (30) contains a quench column and a compression stage with a downstream C3/C4 separation unit for further product separation. Through the C3/C4 separation unit the first product stream (31) is removed which consists of a mainly olefin-containing C3-hydrocarbon fraction with the main component propylene. This can be supplied to a C2/C3-Separation unit for further purification and the contained C3-hydrocarbon fraction to a C3-Splitter, used to separate the desired propylene. The separation units are generally distillation columns.

The second product stream (32) branches off from the C3/C4 separation unit. It mainly consists of a C4+-hydrocarbon fraction with increased paraffin content, as well as remaining oxygenates.

The second product stream (32) is supplied to a second separation stage (40). Here it is configured as a separation column and separates a fraction of high boiling hydrocarbon (42), mainly C7+-hydrocarbon and a hydrocarbon fraction of medium boiling range (43), mainly C5-hydrocarbon, from a resulting third product stream (41).

The hydrocarbon fraction of medium boiling range (43) is to a large extent recirculated to the catalyst of the MTP Reactor (20) through recirculation (45, 91) and a small part is removed from circulation through removal (44). Through direct recirculation, the load on the subsequent separation units is reduced, which leads to economical advantages. Through removal (44), the concentration of individual substances in the circulation is reduced.

The third product stream (41) mainly contains C4- and C5-hydrocarbons as well as olefins and paraffins and the remaining oxygenates.

The third product stream (41) is now fed into an extractive distillation column (50) together with a selective solvent through a solvent recycling (83). N-Methylpyrrolidone (NMP) is used here as selective solvent. Over the top of the extractive distillation column (50) around 90 to 95% pure butane-isomers are extracted as a first paraffin-enriched fraction (51). These are taken for further economic utilization. From the residues of the extractive distillation column (50) a fourth product stream (52) is extracted, which mainly contains C4-olefin and C5-hydrocarbon as well as the solvent. This fourth product stream is taken to a solvent stripper (80), with which the NMP is removed and is taken back to the extractive distillation column through solvent recycling. A solvent purification process can be added to the recirculation in the known manner. The raffinate (81) freed from the solvent (81) from the solvent stripper (80) is now fed back to the catalyst (20) of the MTP Reactor by means of recycling (91) together with the recycling of the hydrocarbon fraction of medium boiling range (45). Through removal (91b), part of the olefin-enriched substance stream can be removed from the recycling (91) and thus from circulation for the purpose of converting the olefins in a further process.

Figure 3:
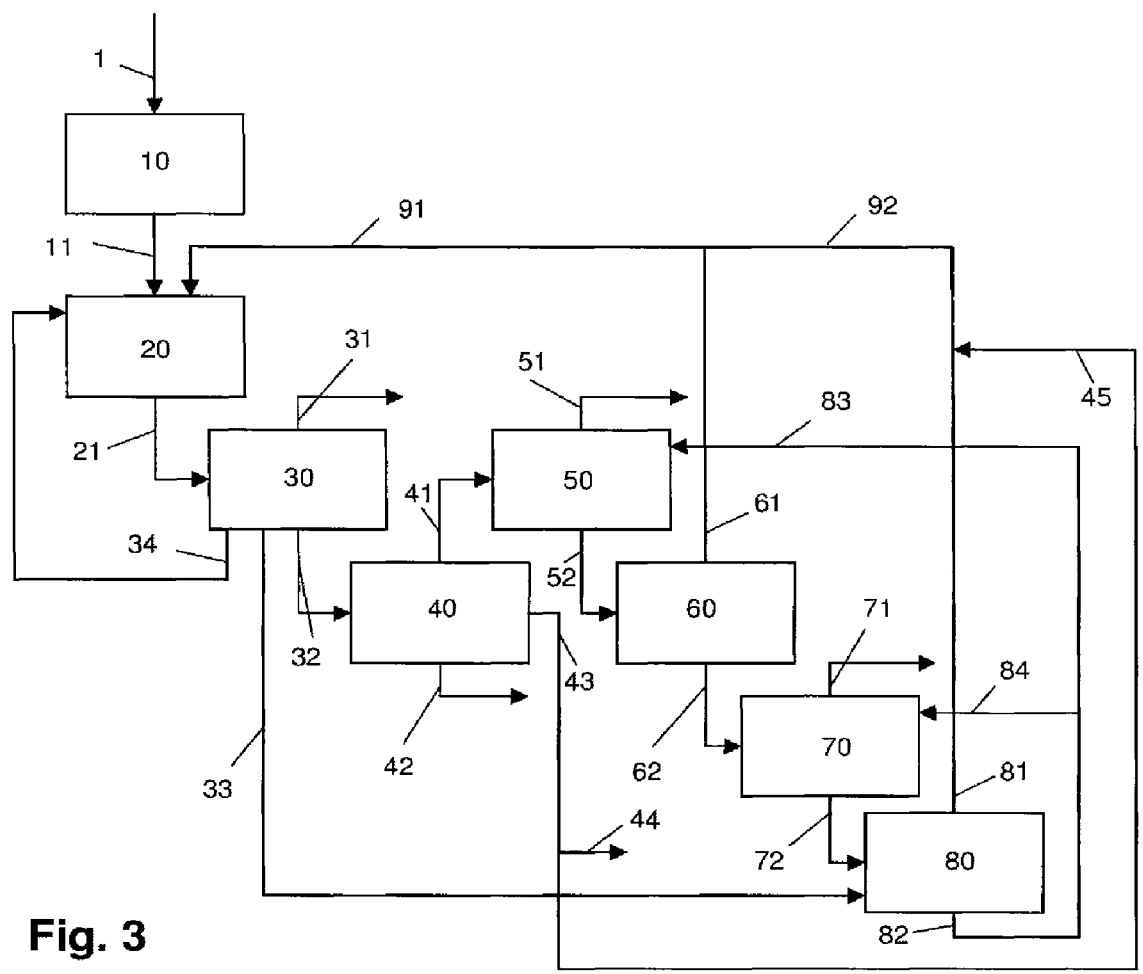

FIG. 3 shows a flow diagram similar to FIG. 2, where two more distillation stages have been added between the extractive distillation columns (50) and the solvent stripper (80), where the first acts as distillation column (60) and the subsequent as second extractive distillation (70).

The fourth product stream (52) is supplied to the distillation column (60) here. Over the top of the distillation column (60) nearly all of the C4-olefin is separated from a first olefin-enriched fraction (61) and fed back to the catalyst of the MTP Reactor (20). The fifth product stream (62) extracted from the residues of the distillation column (60) mainly contains C5-hydrocarbon and is given to the second extractive distillation column (70). From the residues of the second extractive distillation column (70) mainly a part of the C5-paraffins is separated in a second paraffin-enriched fraction (71) and taken out of the circulation. The sixth product stream (72) extracted from the residues of the second extractive distillation column (70) contains a big part of the original C5-olefins and is supplied to the solvent stripper (80).

The solvent stripper (80) removes the solvent from the sixth product stream (72) via residues. The raffinate (81) obtained over the top is fed back to the catalyst (20) of the MTP Reactor via recycling (91, 92).

Water in vapor form can also be added to the solvent stripper (80) in addition to the sixth product stream (72), which is taken from the separation system (30) via pipes (33). Alternatively, the water can be added in liquid form to the second extractive distillation (70). In addition to NMP, ethylene glycol (EG) is added to the solvent circulation. Through the presence of EG and water, the polar oxigenates such as, for example, acetone, ethanol or methyl formate contained in the sixth product stream (62) get bound to EG through the water as solvent maker. As a result, the oxigenates become less volatile and cannot be distilled in the second extractive distillation column (70) over the top with the second paraffin-enriched fraction (71) and taken out of the circulation, but remain in the residues. Because the volatility of the oxygenates is still higher than that of NMP/EG, the said oxigenates are then returned to the catalyst of the MTP Reactor (20) via the top of the solvent stripper (80) with the raffinate (81).

Both exemplary embodiments according to the schematic drawings of FIGS. 2 and 3 are made more precise by use of an example of a mass balance for each.

EXAMPLE 1

The first example shows the separation of a C4-fraction by obtaining Propylene in a configuration with one extractive distillation according to FIG. 2. The separation of a C4-fraction is particularly attractive, because C4-hydrocarbons represent a major part of the reaction mixture (21) and because C4-hydrocarbons come particularly near to the boiling point according to the main product propylene and therefore their separation makes the separation of C3/C4-hydrocarbons noticeably easy.

Table 1 is a mass balance. The streams are arranged according to the reference diagrams. In this configuration 95.4% of the total olefins (98% of C4-olefins) are separated and can be recirculated to the catalyst. With a conventional distillative separation, a comparable total olefin output is about 85-90%.

TABLE 1

Configuration with one extractive distillation unit (FIG. 2)

|  |  | 32 | 41 | 42 | 43 | 44 |
|---|---|---|---|---|---|---|
| H2O | (kg/hr) | 440.7 | 440.6 | 0.0 | 0.0 | 0.0 |
| C3-olefins | (kg/hr) | 182.6 | 182.5 | 0.0 | 0.0 | 0.0 |
| C4-olefins | (kg/hr) | 25502.8 | 21210.8 | 0.5 | 4289.0 | 128.9 |
| C5-olefins | (kg/hr) | 13553.6 | 1701.0 | 43.3 | 11809.1 | 354.8 |
| C6+olefins | (kg/hr) | 4495.3 | 0.0 | 1006.4 | 3488.9 | 104.8 |
| C3-HC | (kg/hr) | 0.0 | 0.0 | 0.0 | 0.0 | 0.0 |
| C4-HC | (kg/hr) | 18375.7 | 14906.8 | 0.5 | 3466.5 | 104.2 |
| C5-HC | (kg/hr) | 112647.6 | 17240.0 | 394.3 | 95012.3 | 2855.0 |
| C6+HC | (kg/hr) | 26669.1 | 0.0 | 7582.2 | 19086.8 | 573.5 |
| Aromatics | (kg/hr) | 15023.1 | 0.0 | 7459.8 | 7563.3 | 227.3 |
| Oxygenates | (kg/hr) | 317.4 | 20.4 | 13.0 | 284.0 | 8.5 |
| NMP | (kg/hr) | 0.0 | 0.0 | 0.0 | 0.0 | 0.0 |
| Mass stream | (kg/hr) | 217208.0 | 55702.2 | 16500.1 | 145000.0 | 4357.0 |
| Temperature | (° C.) | 92.8 | 52.8 | 170.6 | 91.9 | 91.9 |

TABLE 1-continued

Configuration with one extractive distillation unit (FIG. 2)

| | | | | | | |
|---|---|---:|---:|---:|---:|---:|
| Pressure | (bar) | 7.7 | 20.0 | 5.4 | 10.0 | 10.0 |
| Density | (kg/m3) | 558.5 | 561.6 | 622.2 | 564.1 | 564.1 |
| Mol weight | (kg/kmol) | 71.2 | 60.1 | 97.2 | 74.2 | 74.2 |

| | | 45 | 51 | 52 | 81 | 82 | 91 |
|---|---|---:|---:|---:|---:|---:|---:|
| H2O | (kg/hr) | 0.0 | 1.4 | 770.1 | 439.2 | 330.9 | 439.2 |
| C3-olefins | (kg/hr) | 0.0 | 179.7 | 2.9 | 2.9 | 0.0 | 2.9 |
| C4-olefins | (kg/hr) | 4160.2 | 363.4 | 22069.4 | 20845.3 | 1221.4 | 25005.4 |
| C5-olefins | (kg/hr) | 11454.3 | 9.3 | 2214.7 | 1691.9 | 522.7 | 13146.1 |
| C6+olefins | (kg/hr) | 3384.1 | 0.0 | 0.1 | 0.0 | 0.1 | 3384.1 |
| C3-HC | (kg/hr) | 0.0 | 0.0 | 0.0 | 0.0 | 0.0 | 0.0 |
| C4-HC | (kg/hr) | 3362.4 | 5044.5 | 9945.6 | 9860.9 | 83.5 | 13223.3 |
| C5-HC | (kg/hr) | 92157.3 | 101.6 | 19114.2 | 17138.8 | 1974.6 | 109296.1 |
| C6+HC | (kg/hr) | 18513.3 | 0.0 | 0.1 | 0.0 | 0.1 | 18513.3 |
| Aromatics | (kg/hr) | 7336.0 | 0.0 | 0.0 | 0.0 | 0.0 | 7336.0 |
| Oxygenates | (kg/hr) | 275.5 | 0.0 | 35.6 | 20.4 | 15.2 | 295.9 |
| NMP | (kg/hr) | 0.0 | 0.0 | 300000.0 | 0.0 | 300000.0 | 0.0 |
| Mass stream | (kg/hr) | 140643.0 | 5699.9 | 354153.0 | 49999.2 | 304149.0 | 190642.0 |
| Temperature | (° C.) | 91.9 | 66.1 | 124.8 | 30.1 | 173.9 | 71.9 |
| Pressure | (bar) | 10.0 | 10.0 | 10.6 | 10.0 | 15.0 | 10.0 |
| Density | (kg/m3) | 564.1 | 502.2 | 847.3 | 594.4 | 887.5 | 575.8 |
| Mol weight | (kg/kmol) | 74.2 | 57.5 | 90.1 | 60.4 | 98.0 | 70.0 |

EXAMPLE 2

The second example shows the separation of a C4- and a C5-fraction similar to FIG. 3. The main focus lies in the C4-separation, so that the main quantity of the solvent is provided for this.

TABLE 2

Configuration with two extractive distillation units (FIG. 3)

| | | 32 | 41 | 42 | 43 | 44 |
|---|---|---:|---:|---:|---:|---:|
| H2O | (kg/hr) | 410.7 | 410.5 | 0.0 | 0.0 | 0.0 |
| C3-olefins | (kg/hr) | 170.7 | 170.6 | 0.0 | 0.0 | 0.0 |
| C4-olefins | (kg/hr) | 24984.2 | 24980.5 | 0.0 | 0.0 | 0.0 |
| C5-olefins | (kg/hr) | 13200.3 | 10160.9 | 6.1 | 3032.7 | 182.8 |
| C6+olefins | (kg/hr) | 4361.3 | 49.8 | 801.8 | 3509.7 | 211.5 |
| C3-HC | (kg/hr) | 0.0 | 0.0 | 0.0 | 0.0 | 0.0 |
| C4-HC | (kg/hr) | 24911.2 | 24907.4 | 0.0 | 0.0 | 0.0 |
| C5-HC | (kg/hr) | 88607.2 | 70494.7 | 44.1 | 18063.7 | 1088.7 |
| C6+HC | (kg/hr) | 29903.3 | 207.8 | 6538.3 | 23157.2 | 1395.6 |
| Aromatics | (kg/hr) | 9765.6 | 0.1 | 7601.3 | 2164.3 | 130.4 |
| Oxygenates | (kg/hr) | 310.4636 | 229.7 | 8.4 | 7.23E+0 | 4.4 |
| NMP | (kg/hr) | 0.0 | 0.0 | 0.0 | 0.0 | 0.0 |
| Glycol | (kg/hr) | 0.0 | 0.0 | 0.0 | 0.0 | 0.0 |
| Mass stream | (kg/hr) | 196625.0 | 131612. | 15000.0 | 50000.0 | 3013.4 |
| Temperature | (° C.) | 90.2 | 62.4 | 181.0 | 113.8 | 113.8 |
| Pressure | (bar) | 7.7 | 20.0 | 5.4 | 10.0 | 10.0 |
| Density | (kg/m3) | 557.0 | 560.6 | 625.0 | 572.2 | 572.2 |
| Mol weight | (kg/kmol) | 70.1 | 64.8 | 99.4 | 79.9 | 79.9 |

| | | 45 | 51 | 52 | 61 | 62 |
|---|---|---:|---:|---:|---:|---:|
| H2O | (kg/hr) | 0.0 | 13.0 | 4500.8 | 641.3 | 3859.3 |
| C3-olefins | (kg/hr) | 0.0 | 158.5 | 12.1 | 12.1 | 0.0 |
| C4-olefins | (kg/hr) | 0.0 | 60.0 | 24921.1 | 24600.8 | 316.8 |
| C5-olefins | (kg/hr) | 2849.9 | 1.7 | 10415.2 | 5002.4 | 5412.5 |
| C6+olefins | (kg/hr) | 3298.2 | 0.0 | 120.6 | 0.2 | 120.4 |
| C3-HC | (kg/hr) | 0.0 | 0.0 | 0.0 | 0.0 | 0.0 |
| C4-HC | (kg/hr) | 0.0 | 4253.3 | 20654.0 | 20639.9 | 11.0 |
| C5-HC | (kg/hr) | 16975.0 | 14.9 | 70595.5 | 50093.5 | 20499.0 |
| C6+HC | (kg/hr) | 21761.5 | 0.0 | 268.5 | 0.9 | 267.7 |
| Aromatics | (kg/hr) | 2033.9 | 0.0 | 0.3 | 0.0 | 0.3 |
| Oxygenates | (kg/hr) | 67.9 | 0.0 | 1117.4 | 41.8 | 1075.7 |
| NMP | (kg/hr) | 0.0 | 0.0 | 279935.0 | 0.0 | 279935.0 |
| Glycol | (kg/hr) | 0.0 | 0.0 | 5300.3 | 0.0 | 5300.3 |
| Mass stream | (kg/hr) | 46986.6 | 4501.5 | 417841.0 | 101033.0 | 316798.0 |
| Temperature | (° C.) | 113.8 | 62.7 | 113.6 | 44.7 | 111.1 |

TABLE 2-continued

Configuration with two extractive distillation units (FIG. 3)

| Pressure | (bar) | 10.0 | 5.0 | 10.6 | 10.0 | 15.0 |
|---|---|---|---|---|---|---|
| Density | (kg/m3) | 572.2 | 505.9 | 781.3 | 580.6 | 907.4 |
| Mol weight | (kg/kmol) | 79.9 | 57.0 | 81.7 | 63.3 | 90.1 |

|  |  | 71 | 72 | 81 | 82 | 33 |
|---|---|---|---|---|---|---|
| Mass stream | (kg/hr) |  |  |  |  |  |
| H2O | (kg/hr) | 42.6 | 4239.7 | 712.8 | 4526.9 | 1000.0 |
| C3-olefins | (kg/hr) | 0.0 | 0.0 | 0.0 | 0.0 | 0.0 |
| C4-olefins | (kg/hr) | 66.1 | 250.6 | 249.6 | 0.8 | 0.0 |
| C5-olefins | (kg/hr) | 318.7 | 5120.0 | 4836.6 | 282.4 | 0.0 |
| C6+olefins | (kg/hr) | 0.1 | 127.6 | 49.5 | 78.1 | 0.0 |
| C3-HC | (kg/hr) | 0.0 | 0.0 | 0.0 | 0.0 | 0.0 |
| C4-HC | (kg/hr) | 4.0 | 7.0 | 7.0 | 0.0 | 0.0 |
| C5-HC | (kg/hr) | 3336.8 | 17171.2 | 17036.4 | 127.5 | 0.0 |
| C6+HC | (kg/hr) | 24.2 | 249.7 | 182.7 | 67.0 | 0.0 |
| Aromatics | (kg/hr) | 0.0 | 0.3 | 0.1 | 0.3 | 0.0 |
| Oxygenates | (kg/hr) | 3.7 | 1163.6 | 184.2 | 979.3 | 0.0 |
| NMP | (kg/hr) | 0.0 | 308821.0 | 0.0 | 308821.0 | 0.0 |
| Glycol | (kg/hr) | 0.0 | 5847.3 | 0.0 | 5847.3 | 0.0 |
| Mass stream | (kg/hr) | 3796.2 | 342998.0 | 23258.8 | 320730.0 | 1000.0 |
| Temperature | (° C.) | 52.4 | 117.8 | 27.7 | 169.9 | 200.0 |
| Pressure | (bar) | 5.0 | 3.6 | 5.0 | 15.0 | 2.0 |
| Density | (kg/m3) | 594.9 | 910.8 | 637.4 | 898.8 | 0.9 |
| Mol weight | (kg/kmol) | 69.3 | 90.5 | 65.4 | 91.9 | 18.0 |

|  |  | 83 | 84 | 91 | 92 |
|---|---|---|---|---|---|
| Mass stream | (kg/hr) |  |  |  |  |
| H2O | (kg/hr) | 4103.4 | 423.4 | 1354.1 | 712.9 |
| C3-olefins | (kg/hr) | 0.0 | 0.0 | 12.1 | 0.0 |
| C4-olefins | (kg/hr) | 0.7 | 0.1 | 24850.4 | 249.6 |
| C5-olefins | (kg/hr) | 256.0 | 26.4 | 12688.9 | 7686.5 |
| C6+olefins | (kg/hr) | 70.8 | 7.3 | 3347.9 | 3347.7 |
| C3-HC | (kg/hr) | 0.0 | 0.0 | 0.0 | 0.0 |
| C4-HC | (kg/hr) | 0.0 | 0.0 | 20646.9 | 7.0 |
| C5-HC | (kg/hr) | 115.6 | 11.9 | 84104.8 | 34011.4 |
| C6+HC | (kg/hr) | 60.7 | 6.3 | 21945.1 | 21944.2 |
| Aromatics | (kg/hr) | 0.2 | 0.0 | 2033.9 | 2033.9 |
| Oxygenates | (kg/hr) | 887.7 | 91.6 | 293.9 | 252.2 |
| NMP | (kg/hr) | 279935.0 | 28886.0 | 0.0 | 0.0 |
| Glycol | (kg/hr) | 5300.3 | 546.9 | 0.0 | 0.0 |
| Mass stream | (kg/hr) | 290750.4 | 30000.0 | 171283.6 | 70251.4 |
| Temperature | (° C.) | 107.4 | 107.4 | 59.1 | 79.6 |
| Pressure | (bar) | 13.8 | 13.8 | 5.0 | 5.0 |
| Density | (kg/m3) | 958.0 | 958.0 | 587.3 | 600.7 |
| Mol weight | (kg/kmol) | 91.9 | 91.9 | 67.4 | 74.5 |

| List of reference figures: | |
|---|---|
| 1 | Methanol |
| 10 | DME Reactor |
| 11 | First Reaction Mixture |
| 20 | Catalyst in the MTP Reactor |
| 21 | Second Reaction Mixture |
| 300 | Separation System |
| 321 | Paraffin-enriched Fraction |
| 322 | Remaining Product Stream |
| 30 | First Separation Stage |
| 31 | First Product Stream |
| 32 | Second Product Stream |
| 33 | Water for Oxygenate Separation |
| 34 | Water for Recycle in MTP Reactor |
| 40 | Second Separation Stage |
| 41 | Third Product Stream |
| 42 | Higher Boiling Hydrocarbon |
| 43 | Hydrocarbon Fraction of Medium Boiling Range |
| 44 | Separation of Hydrocarbon Fraction of Medium Boiling Range |
| 45 | Recycling of Hydrocarbon Fraction of Medium Boiling Range |
| 500 | Paraffin-Olefin Separation Stage |
| 50 | Extractive Distillation |
| 51 | First Paraffin-Enriched Fraction |
| 52 | Fourth Product Stream |
| 60 | Distillation |
| 61 | First Olefin-Enriched Fraction |
| 62 | Fifth Product Stream |
| 70 | Second Extractive Distillation |
| 71 | Second Paraffin-Enriched Fraction |
| 72 | Sixth Product Stream |
| 80 | Solvent Stripper |
| 81 | Raffinate |
| 82 | Solvent |
| 83 | Solvent Flow Back in the First Extractive Distillation |
| 84 | Solvent Flow Back in the Second Extractive Distillation |
| 91, 82 | Recycling |
| 91b | Removal |

The invention claimed is:

1. A method for manufacturing at least one lower olefin from an oxygenate-containing first reaction mixture (11) through conversion at a catalyst (20) to an olefin and paraffin-containing second reaction mixture (21), which is fed to a first separation stage (30), in which at least one lower olefin-containing first product stream (31) and one higher olefin and paraffin-containing second product stream (32) are separated, wherein the second product stream (32) is further separated into a higher boiling hydrocarbons stream (42) and a third product stream (41) in a second separation stage (40), the third product stream (41) is fed to an extractive distillation unit (50) wherein a paraffin-enriched fraction (51) is extracted by means of a selective polar solvent to leave a fourth product stream (52), which is fed to a solvent stripper (80) where solvent is removed from said fourth product stream (52) and recycled to the extractive distillation (50), leaving a rafinate (81) which is at least partially recirculated to the catalyst (20).

2. A method according to claim 1, further comprising the step of extracting a hydrocarbon fraction of middle boiling range (43) from the second product stream (32) through the second separation stage (40), so that this is not recirculated to the catalyst (20) or is only partially recirculated to the catalyst (20).

3. A method according to claim 1 wherein before the fourth product stream (52) is fed to solvent stripper (80) a first olefin-enriched fraction (61) is extracted from the fourth product stream (52) through a further distillation (60), leaving a fifth product stream (62), and a second paraffin-enriched fraction (71) is extracted from the fifth product stream (62) through a second extractive distillation (70) by means of a selective polar solvent to form a sixth product stream (72), which is then fed to solvent stripper (80).

4. A method according to claim 3 where the solvent in the product streams after the first and second extractive distillations (50, 70) is recovered with solvent stripper (80) after the second extractive distillation (70) from the sixth product stream (72) and is recirculated (83,84) to the first and second extractive distillation by the solvent stripper.

5. A method according to claim 1, wherein the selective polar solvent is N-Methylpyrrolidone.

6. A method according to claim 3, wherein ethylene glycol and water are added to the selective polar solvent.

7. A method according to claim 6 where the added water (33) is extracted from the first separation stage (30).

8. A method according to claim 1, wherein the oxygenates in the first reaction mixture contain dimethylether and water.

9. A method according to claim 1, wherein the catalyst (20) for the first reaction mixture (11) is a form-selective Zeolite catalyst of the Pentasil type.

10. A method according to claim 1, wherein said lower olefin is propylene and the first reaction mixture (11) is created from methanol (1) at least partially by means of a dehydrating catalyst (10).

11. A method according to claim 2 wherein from the fourth product stream (52) a first olefin-enriched fraction (61) is extracted through a further distillation (60) and from the remaining fifth product stream (62) a second paraffin-enriched fraction (71) is extracted through a second extractive distillation (70, 80) by means of a selective polar solvent and where the sixth product stream (72) remaining after the removal of the solvent as well as the first olefin-enriched fraction (61) is recirculated to the catalyst (20) at least partially (91).

12. A method according to claim 11 where the solvent in the product streams after the first and second extractive distillation (50, 70) is recovered with a common solvent stripper (80) after the second extractive distillation (70) from the sixth product stream (72) and is recirculated to the first and second extractive distillation by the common solvent stripper (83, 84).

13. A method according to claim 4, wherein ethylene glycol and water are added to the selective polar solvent.

14. A method according to claim 11, wherein ethylene glycol and water are added to the selective polar solvent.

15. A method according to claim 12, wherein ethylene glycol and water are added to the selective polar solvent.

16. A method according to claim 13 where the added water (33) is extracted from the first separation stage (30).

17. A method according to claim 14 where the added water (33) is extracted from the first separation stage (30).

18. A method according to claim 15 where the added water (33) is extracted from the first separation stage (30).

19. A method according to claim 1 the oxygenates in the first reaction mixture contain dimethylether and water.

20. A method according to claim 1, wherein the catalyst (20) for the first reaction mixture (11) is a form-selective Zeolite catalyst of the Pentasil type.

21. A method according to claim 1, wherein said lower olefin is propylene and the first reaction mixture (11) is created from methanol (1) at least partially by means of a dehydrating catalyst (10).

* * * * *